United States Patent [19]

Glazier

[11] Patent Number: 5,274,162
[45] Date of Patent: Dec. 28, 1993

[54] ANTINEOPLASTIC DRUGS WITH BIPOLAR TOXIFICATION/DETOXIFICATION FUNCTIONALITIES

[76] Inventor: Arnold Glazier, 9 Brandeis Rd., Newton, Mass. 02159

[21] Appl. No.: 808,030

[22] Filed: Dec. 13, 1991

[51] Int. Cl.$^5$ .............. A01N 47/16; A01N 41/02; A01N 37/34; A61K 31/445; C07F 9/02
[52] U.S. Cl. ............................ 558/166; 514/118; 514/553; 514/603; 514/114; 558/169; 558/170; 558/171; 558/172; 562/67; 564/85; 564/94
[58] Field of Search .............. 514/118, 553, 603; 558/166, 169, 170, 171, 172; 562/67; 564/85, 94

[56] References Cited

U.S. PATENT DOCUMENTS

| | | | |
|---|---|---|---|
| 2,120,808 | 6/1938 | Lecher | 562/67 |
| 3,035,080 | 5/1962 | Arnold et al. | 558/166 X |
| 3,769,406 | 10/1973 | Anatol et al. | 514/118 |
| 4,154,826 | 5/1979 | Rathgeb | 514/118 X |
| 4,165,258 | 8/1979 | Pye et al. | 564/94 X |
| 4,723,029 | 2/1988 | Vashi et al. | 562/67 X |
| 5,055,459 | 10/1991 | Anderson et al. | 514/118 X |
| 5,091,394 | 2/1992 | Englert et al. | 514/603 X |

FOREIGN PATENT DOCUMENTS 52-19654  2/1977  Japan ..................... 564/94

Primary Examiner—Floyd D. Higel
Attorney, Agent, or Firm—Hamilton, Brook, Smith & Reynolds

[57] ABSTRACT

The composition, methods of synthesis, and applications of a new class of tumor selective antineoplastic drugs is described. These novel antineoplastic agents are of the general structure: A-C-B. The agents are designed with two key functionalities: a trigger which toxifies the drug; (A) and a deactivator which detoxifies the drug (B) The trigger is selected such that it is activated by an enzyme which is present in elevated levels in the tumor. The deactivator is selected such that it is actuated by an enzyme ubiquitous to all tissues. The fate of the drug in a given cell is then determined by the ratio of the enzymatic activity that triggers toxication to the enzymatic activity which detoxifies the drug. The partitioning of the drug between toxic metabolite and nontoxic metabolite defines the resulting specificity of cytotoxic effect. The application of this invention is exemplified by a new class of antineoplastic drugs which are designed to be selectively toxic for tumor cells bearing the enzyme guanidinobenzoatase.

8 Claims, No Drawings

5,274,162

ANTINEOPLASTIC DRUGS WITH BIPOLAR TOXIFICATION/DETOXIFICATION FUNCTIONALITIES

TECHNICAL FIELD

This invention is in the fields of chemistry, medicine and pharmacology.

BACKGROUND

An enzymatic activity unique to neoplastic cells remains elusive. However, important quantitative differences in enzyme activity between normal and malignant tissues are well known. Knox, W. E. (1976) *Enzyme Patterns in Fetal, Adult, and Neoplastic Rat Tissue;* S. Karger Basil. Switzerland. These differences form the basis for the selectivity of currently employed antineoplastic drugs. Alkylating agents are among the most potent and toxic anticancer drugs currently in clinical use. The oncospecificity of alkylating agents resides largely in the increased susceptibility of the DNA of rapidly proliferating cells to alkylation. Other factors such as differences in protective glutathione levels and DNA repair activity are also important.

Despite the major advances in clinical cancer therapy due to alkylating agents, drugs of this class have severe limitations. The major problem is one of nonspecific toxicity. There have been numerous attempts to develop alkylating agents which are selectively targeted to tumor cells. Thousands of derivatives have been synthesized and tested for selective antitumor activity. With few exceptions the results have been uniformly discouraging. For example, alkylating agents which are activated by enzymes present in tumor tissue such as alkaline phosphatase, azo-reductase, glucuronidase, plasmin, and collagenase have been explored. Ross, W. C.; Warwick, G. P.; Roberts, J. J.; *J. Chem. Soc,* 3100 (1955). Connors, T. A.; Foster, A. B., Tisdale, M. J.; (1972) *Biochem, Pharmacol,* 21:1309 . Connors, T. A.; Whisson, M. E.; (1966) *Nature* 210:866 Ball, C. R.; Double, J. A.; (1974) *Biochem, Pharmacol* 23:3173. Workman, P.; Double, J. A.; (1977) *Biochem, Pharmacol,* 27:199. Marquissee, M. J.; Kauer, J. C. (1978); *J. Med. Chem.;* 21:1188 Chakravarty, P.; Carl, P.; Weber, M.; Katzenenellenbogen, J.; (1983); *J. Med. Chem.:* 26:633; and 26:638 The fundamental problem remains one of tumor specificity. Although the tumor may have many fold higher levels of the target enzyme normal tissues also invariably possess some of the enzyme which ultimately activates the alkylating agent and results in toxicity. This severely limits tumor selectivity.

SUMMARY OF THE INVENTION

This invention relates to a new class of tumor selective antineoplastic agents. These novel antineoplastic agents are designed with two key functionalities: a trigger which toxifies the drug; and an deactivator which detoxifies the drug. The trigger is selected such that it is activated by an enzyme which is present in elevated levels in the tumor. The deactivator is selected such that it is actuated by an enzyme ubiquitous to all tissues. The fate of the drug in a given cell is then determined by the ratio of the enzymatic activity that triggers toxication to the enzymatic activity which detoxifies the drug. The partitioning of the drug between toxic metabolite and nontoxic metabolite defines the resulting specificity of cytotoxic effect. The application of this invention is exemplified by a new class of antineoplastic drugs which are designed to be selectively toxic for tumor cells bearing the enzyme guanidinobenzoatase.

DETAILED DESCRIPTION OF THE INVENTION

General Structure

This invention is a new class of tumor selective antineoplastic agents. These novel antineoplastic agents consist of two key functionalities: a trigger which toxifies the drug; and an deactivator which detoxifies the drug. The trigger is selected such that it is activated by an enzyme which is present in elevated levels in the tumor. The deactivator is selected such that it is actuated by an enzyme ubiquitous to all tissues. The fate of the drug in a given cell is then determined by the ratio of the enzymatic activity that triggers toxication to the enzymatic activity which detoxifies the drug. The partitioning of the drug between toxic metabolite and nontoxic metabolite defines the resulting specificity of cytotoxic effect. In normal tissues with low levels of the triggering enzyme the drug is largely detoxified. In tumor cells with high levels of the triggering enzyme a high percentage of the drug is activated to a cytotoxin. Oncospecificity is further enhanced by selection of a toxic species which itself also has preferential toxicity for malignant cells. The deactivator functionality may also be designed such that it is actuated independently of enzymes in a spontaneous fashion. In this case the deactivator serves as an internal clock. Oncospecificity results directly from quantitative differences in the levels of triggering enzyme in tumor versus normal tissues. The general structure of bipolar antineoplastic drugs is shown below:

A-C-B

Wherein A is selected to be a substrate for an enzyme (Ea) which is enriched in the target tumor such that the action of this enzyme on A toxifies the drug. B is selected to be a substrate for one or more enzymes (Eb) which are present in normal tissues such that the enzymatic activity of this enzyme actuates detoxification of the drug. C represents that portion of the drug molecule which may be activated to a toxic species or deactivated. Oncospecificity results from the spectrum of partitioning of the drug between toxification and detoxification.

A wide variety of tumor "selective" enzymes may be chosen to trigger drug toxication. The toxication may arise from an enzymatically induced increase in chemical reactivity and (or) from an enzymatic transformation which enhances drug uptake into the tumor cells.

In this patent application we focus on antineoplastic drugs which are activated by a cell surface tumor associated enzyme: Guanidinobenzoatase (GB). GB is a serine protease which catalyzes the cleavage of the arginyl bond in the peptide GlyArgGlyAsp. This peptide sequence is critical to cell attachment to fibronectin. GB also catalyzes the cleavage of p-nitrophenol Guanidinobenzoate. The active enzyme is present on the surface of most types of malignant cells examined in man, mouse, rat, dog and rabbit.(Frank S. Steven personal communication (1991) ) Selective stains for GB have been employed with striking success to identify malignant cells in pathology specimens. GB is also present on the surface of normal cells that are capable of migration and on the surface of normal colonic epithelial cells. GB appears to be similar if not identical to single chain tissue plasminogen activator. A unique feature of GB is the enzymes ability to cleave p-nitrophenol guanidinobenzoate and 4-methylumbelliferyl-guanidinobenzoate. Other serine proteases are inactivated by these substrates. There are no known anticancer drugs which are toxic on the basis of targeting for cells that express GB.

Steven, F. S.; Al-Ahmad, R. K.; (1983) *Eur. J. Biochem.;* 130:335

Steven, F. S.; Al-Ahmad, R. K.; (1985) *Eur. J. Biochem.;* 149:35

Steven, F. S.; Griffin, M. M.; Maier, H.; Talbot; I. C.; (1990) *Biol. Chem. Hoppe-Seyler;* 371:89

Steven, F. S.; Griffin, M. M.; (1988) *Biol. Chem. Hoppe-Seyler;* 369:137

Steven, F. S.; Ali, H.; Griffin, M. M.; (1988) *Br. J. Cancer;* 57:160

Steven, F. S.; Johnson, J.; (1990); *Biochem. Soc. Trans;* 18:632

Steven, F. S.; Griffin, M. M.; (1990); *Biochem. Soc. Trans;* 18:632

Perry, J.; Scott, G. K.; (1990); *Biosci. Rep.;* 10:469

Steven, F. S.; Griffin, M. M.; et.al.; (1991); *Anticancer Res.;* 11:641

Steven, F. S.; Griffin, M. M.; et.al.; (1991); *Anticancer Res.;* 11:1189

Steven, F. S.; Zoeller, J.; Maier, H.; Born, I. A.; (1991) *J. Enzyme Inhibition;* 5:151

Steven, F. S.; Griffin, M.; Williams, L., Clark, N.; Maier, H.; (1991) *J. Enzyme Inhibition;* 4:337

Steven, F. S.; Jackson, N.; Wong, T.; (1987); *Br. J. Cancer;* 55:29

Steven, F. S.; Griffin, M. M.; et.al.; (1988); *Anticancer Res.;* 8:1179

Chase, T.; Shaw, E.; (1967); *Biochem. Biophys. Res. Comm.;* 29:508

Steven, F. S.; Maier, H.; (1989); *Biochem. Soc. Trans.;* 17:1125

Geiger, M.; Binder, B.; (1987); *Biochem. biophys. Acta;* 912:34

Fasco, M.; Fenton, J.; (1973); *Arch. Biochem. Biophys.;* 159:802

The present class of GB selective antineoplastic drugs are designed such that the enzymatic activity of tumor associated GB triggers the production of a potent bifunctional alkylating agent. This alkylating agent then kills the tumor cells by cross linking DNA or by inactivating vital enzymes. A wide variety of bifunctional alkylating agents may be employed. The key requirement is that the reactivity or cytotoxicity of the alkylating agent should be dramatically enhanced directly or indirectly by the cleavage of an ester or amide functionality by the enzyme GB. This enhancement in toxicity may result from enhanced chemical reactivity of the alkylating agent and (or) by increased cellular uptake of the toxic species. For example, the chemical reactivity of substituted aniline mustard is known to be a function of the Hammett sigma constituents of the substitutents. Electron donating substituents increase reactivity and toxicity. Panthanananickal, A.; Hansch, C.; Leo, A.; (1978) *J. Med. Chem,;* 21:16. P-hydroxyaniline mustard is expected to be more toxic to cells the its corresponding p-guanidinobenzoate ester. The enhanced toxicity will be due to a higher chemical reactivity and an increased rate of diffusion into cells. Consequently GB would be expected to toxify the guanidinobenzoate ester of p-hydroxyaniline mustard by cleaving the ester and liberating the more toxic p-hydroxyaniline mustard.

In the preferred embodiment of this invention the drug is designed such that GB triggers the activation and release of a phosphoramide type mustard derivative by cleaving an appropriately located amide of ester functionality. Activated phosphoramide mustard derivatives are the toxic species which mediated the anticancer effects of cyclophosphamide and ifosfoamide. Freidman, O.; Myles, M.; Colvin, M. (1979) *Advances in Cancer Chemotherapy;* 1:143. Boyd, V.; Robbins, J.; Egan, W.; Ludeman, S.; (1986); *J. Med. Chem.;* 29:1206 Compounds such as cyclophosphamide, ifosfoamide, and benzylic esters of phosphoramide mustard are not active alkylating agents. In the absence of biotransformation these compounds are relatively nontoxic. The electron withdrawing influence of the phosphorus atom dramatically depresses the ability of the adjacent nitrogen to attack the chloro-ethyl group and produce an aziridinium cation. However, conversion of the phosphoester group of compounds such as cyclophosphamide, ifosfoamide, and esters of phosphoramide mustard to a negatively charged species enormously increases the nucleophilicity of the adjacent nitrogen. This triggers the formation of the highly toxic aziridinium cation. Brock, N. (1976); *Cancer Treatment Rep.;* 12:301. Kwon, C.; Moon, K.; Baturay, N.; Shirota, F.; (1991); *J. Med. Chem.;* 34:588.

A number of enzymes may be selected to actuate the detoxification of the GB selective drugs. The key requirement is that the enzyme selected should be present in normal tissues and capable of detoxifying the phosphoramide mustard. In the preferred embodiment of the detoxification mechanism a nucleophile is unmasked by the detoxifying enzyme and reacts intramolecularly with the aziridinium cation. This will preclude the alkylation of DNA and vital cellular enzymes.

The intramolecular nucleophilic opening of an aziridinium type cation must proceed via a transition state in which the carbon atom assumes a bipyramidal-trigonal geometry with the nucleophile and departing nitrogen occupying apical positions. If linearity between the nucleophile and the departing group can not be achieved the reaction will not proceed. Tenud, L.; Farooq, S.; Seibel, J.; Eschenmoser, A.; (1970) *Helv. Chim. Acta.;* 53:2059. For example, aniline mustard derivatives with an ortho carboxylate group are potent and toxic alkylating agents. Because of the inability to assume the prerequisite transition state geometry the carboxylate group is unable to react intramolecularly and detoxify the aziridinum cation. Niculescu-Duvaz, I.; Feyns, V.; Dobre, V.; (1978)

Cancer Treatment Rep.; 62:2045.

In the preferred embodiments of the detoxification mechanism the detoxifying enzyme unmasks a nucleophile which is positioned such that it will react intramolecularly with the aziridinium cation to form a 5 membered ring and concomitantly open the aziridium ring as shown below:

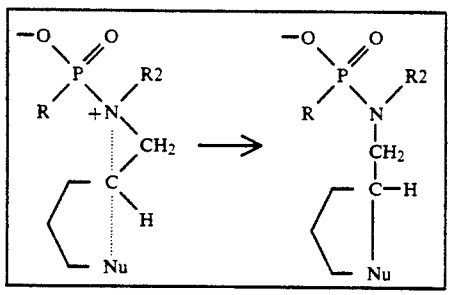

The nucleophile (Nu) may be any group such as a hydroxy, thiol, amine, or carboxylate moiety. A key requirement is that the nucleophile should be unmasked by an enzyme which is ubiquitous to normal tissues but not by the tumor selective toxifying enzyme. For example, hydroxy groups and carboxylate groups can be masked as esters which may be cleaved by ubiquitous nonspecific esterase. Amino groups can be masked as amides or as azo moieties which can be unmasked respectively by proteases or azoreductases. Thiols can be masked as thio-esters or disulfides. Thiol esters can be cleaved by thiol-esterases. Disulfides can be reduced to thiols by a variety of enzymatic processes. The deactivator functionality may also be selected such that it is activated independently of enzymes. The nucleophile may be masked as a functionality which undergoes spontaneous nonenzymatic transformation to yield the exposed nucleophile. In this case the detoxification mechanism functions as an internal clock. Oncospecificity will result directly from quantitative differences in the levels of triggering enzyme in tumor versus normal tissues. For example, a hydroxy group could be masked as an enol ether. An amino group could be masked as an enamine.

In the preferred embodiment of the class of GB selective antineoplastic drugs invention the detoxification mechanism is actuated by the enzymatic activity of nonspecific esterase. GB is present on the surface of normal colon epithelial cells. However, these cells also possess high levels of nonspecific esterase activity. Thus by selecting esterase as a detoxifying enzyme we can ameliorate the effects of the drug on normal colonic cells. The esterase exposes a hydroxy group which is suitably located to react intramolecularly with the aziridinium cation to effect detoxification.

Normal colonic GB may be inactivated by the oral administration of a nonabsorbable inhibitor of the enzyme GB.

The general structure for one class antineoplastic drugs which is selectively toxic for Guaninidobenzoatase+tumor cells is shown below as Formula 1:

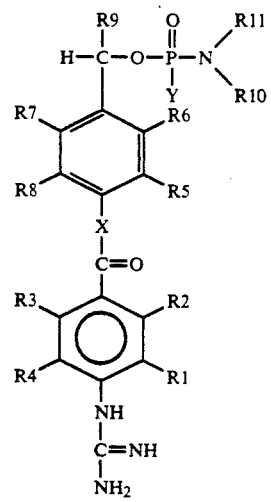

FORMULA 1

Wherein R1,R2,R3,R4, may each be selected from the group: (H,Cl,F, Br; methyl, or —O—CH3); X may be O, or NH; R5,R6,R7, and R8 may be selected from the group: (H; Cl; F; CH3; — O-CH3; —NO2); R9 is H or —CH2—CO2—R13, R13 is methyl, or ethyl, R10 is —CH2—CHClR14, or —CHR14—CH2—Cl R11 is H; —CH2—CHClR14; —CHR14—CH2—Cl; or —CH3 Y is —NH3; —NH—CH2—CHClR14; —NH—CHR-14—CH2—Cl; —OCH3; —CH3;

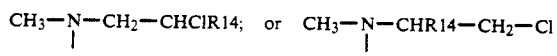

And wherein the total number of chlorine atoms attached to groups Y, R10 and R11 is equal to 2, 3, or 4. And wherein R14 is selected from the group: ( H; —CH2—CH2—CH2—O—CO—R15; —CH2—CH2—CH2—NH—CO—R15; —CH2—CH2—CH2—S—CO—R15); wherein R15 is a methyl, ethyl, isopropyl, butyl, phenyl, or is selected such that HO—CO—R15 is an amino acid Some preferred embodiments of these GB selective antineoplastic drugs is shown below as Formulae 2:

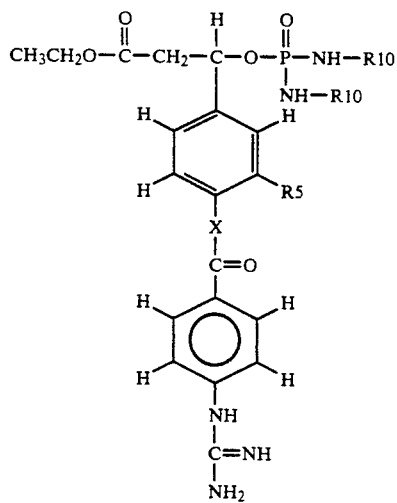

FORMULA 2

Wherein X is O, or NH; R5 is H or a halogen; and R10 is selected from the following group:

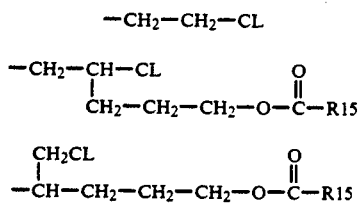

Wherein R15 is as described for Formula 1.

Mechanism of Action

Compounds given by Formula 1 will be converted into a potent cytotoxin by the action of the enzyme GB which is present on the surface of tumor cells. GB will selectively cleave the guanidinobenzoate ester or guanidinobenzamide moiety and liberate at the surface of the tumor cell an intermediate of the following structure shown as Formula 3:

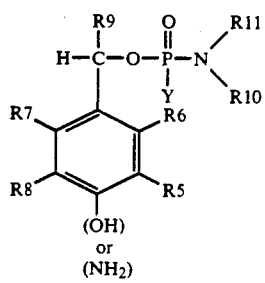

FORMULA 3 this neutrally charged intermediate will rapidly diffuse into and across the tumor cell membrane. The strongly electron donating para-hydroxy or para-amino group which is unmasked by GB in turn will trigger the heterolytic cleavage of the benzylic phospho-ester. The net effect will be to generate both intra and extracellularly the following species shown as Formula 4:

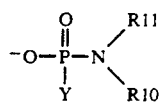

FORMULA 4 which will undergo rapid cyclization to form a highly toxic aziridinium type cation.

For a detailed discussion of the chemical mechanisms involved in the heterolytic cleavage of the C—O bond to liberate the compound shown as Formula 4 see U.S. patent application Ser. No. 07/714,130 titled *Phosphorous Predrugs* filed by A. Glazier. The rate at which the C—O bond of a compound of Formula 1 undergoes heterolytic cleavage is a function of the Hammett sigma+constituents on the benzene ring. Electron donating substituents dramatically increase the rate of solvolysis. Cleavage of the ester or amide functionality by GB unmasks respectively a para-hydroxy or p-amino group. These groups are strongly electron donating and enormously accelerate the rate of spontaneous solvolysis.

The metabolism of the antineoplastic drug in normal tissues will follow a different course. Normal cellular enzymes will detoxify the drug by cleaving the ester or amide functionalities present on R10, R11, or Y. This will expose an intramolecular nucleophile which is favorably positioned to capture and detoxify an aziridinium ion that may form. The net effect is that in tissues low in GB activity the drug will be detoxified.

Detoxification will also occur in tumor tissues. However, once a molecule of drug has been cleaved by GB it will no longer be susceptible to detoxification. The short half life of the toxic intermediates given by Formula 3 and Formula 4 will preclude significant detoxification by nonspecific esterase.

In compounds given by Formula 1 the specificity for GB is provided by the positively charged guanidino moiety. Other positively charged groups or analogs of the guanidino moiety will also function. These are to be considered within the scope of the present invention. One skilled in the arts will recognize other compounds which are activated by the enzymatic activity of GB to yield a cytotoxin. These are to be considered within the scope of the present invention.

The drugs can be administered orally, parenterally or topically. The form in which the drugs are given (e.g., powder, tablet, capsule, solution, emulsion) will depend upon the route by which it is to be administered. The quantity of the drugs to be administered will be determined on an individual basis and will be determined in part on consideration of the individuals size, the severity of the symptoms, and the result sought.

The composition of the present invention can optionally include, in addition to the prodrug other components. The other components included in a particular composition are determined primarily by the route of administration. For example, a composition to be administered orally in tablet form can include, in addition to the drug, a filler (e.g., lactose), a binder (e.g. carboxymethyl cellulose, gum arabic, gelatin) a flavoring agent, a coloring agent, and a coating material (e.g., wax, or a plasticizer). A composition to be administered in a liquid form can include the drugs of the present invention, and optionally an emulsifying agent, a carrier (e.g. saline or water), a flavoring agent, and or a coloring agent. A composition to be administered in a topical form may include an emulsifying agent, a solvent, stabilizing agents and a base such as polyethylene glycol. The preferred route of administration is intravenously.

In the preferred method of use the GB selective antineoplastic drug is given intravenously. To inhibit normal colonic GB activity the patient is pretreated with an oral nonabsorbable inhibitor of GB.

Nonabsorbable Inhibitors of GB

Normal colonic epithelium does have GB activity. To ameliorate nonspecific GI toxicity the surface GB activity of colonic epithelial cells may be selectively inhibited by the oral administration of an enzyme inhibitor for GB which is not absorbed. The inhibitor consists of 3 parts: a cationic site such as a guanidino moiety; a site which resembles the tetrahedral transition state of ester hydrolysis; and a carrier which precludes drug absorption. The carrier portion may impede drug absorption by virtue of being electrically charged and (or) by being a large hydrophilic moiety.

The structure of one class of orally nonabsorbable GB inhibitors is shown below as Formulae 5:

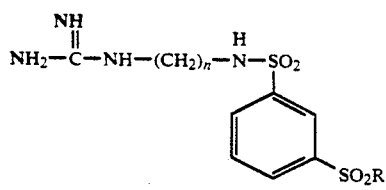

FORMULAE 5

Wherein n=3, 4, or 5. R may be OH (or its sodium or potassium salt). R may be hydrophilic carrier moiety such as polyethylene glycol. R may also be a group such as: guanidino-(CH2)n—NH—. A necessary requirement for the carrier is the presence of an amino or hydroxy group to couple with the sulfonyl group.

EXAMPLE 1

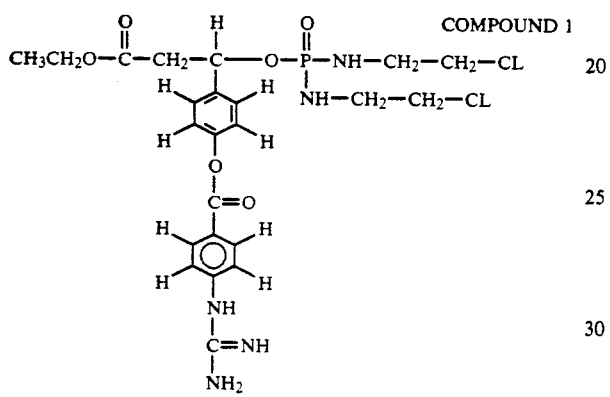

COMPOUND 1

Compound 1 shown above will be selectively toxic for tumor cells which express cell surface guanidinobenzoatase activity. Cleavage of the guanidinobenzoate ester will liberate at the cell surface the following labile intermediate:

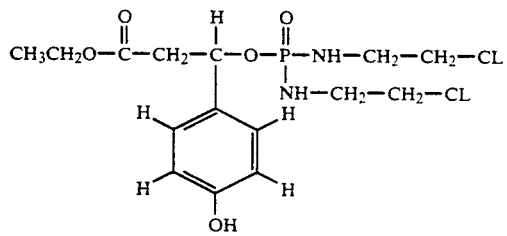

This neutrally charged lipophilic intermediate will rapidly diffuse into and through the tumor cell membrane. The intermediate will undergo a rapid spontaneous elimination reaction to yield ethyl 4-hydroxycinnamate and the following species:

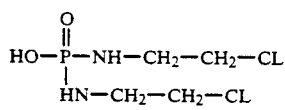

isophosphoramide mustard which is a potent bifunctional alkylating agent.

SYNTHESIS OF COMPOUND 1

The antineoplastic drug shown as Compound 1 may be synthesized as follows: p-guanidinobenzoic acid is refluxed with thionyl chloride to yield the corresponding p-guanidinobenzoic acid chloride. This is then reacted with ethyl p-hydroxybenzoylacetate in the presence of a catalyst such as dimethylaminopyridine (DMAP) to yield Compound 2 of the following structure:

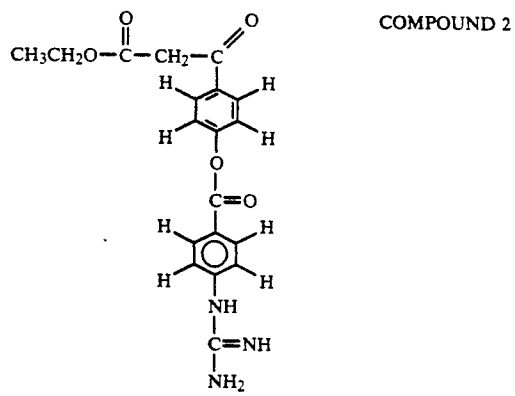

COMPOUND 2

Compound 2 is then reduced to the alcohol shown below as Compound 3. This reduction may be effected by a variety of reagents such as ammonia-borane, or catalytic hydrogenation with platinum dioxide. Enantioselective reduction may be effected by catalytic hydrogenation with a chiral Noyori catalyst. Noyori, R.; Ohkuma, T.; Kitamura, M.; (1987); *J. Am. Chem. Soc.;* 109:5856 Taber, D. F.; Silverberg, L.; (1991); *Tetrahedron Lett.;* 32:4227

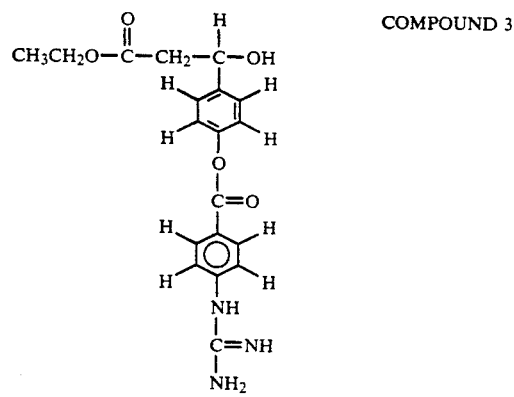

COMPOUND 3

Compound 3 is then reacted with Compound 4 shown below) in the presence of a suitable catalyst such an n-methylimidazole to yield the drug (Compound 1) which is isolated as the HCL salt.

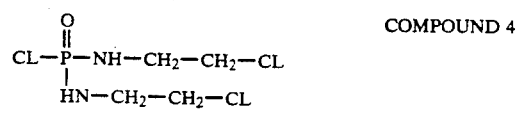

COMPOUND 4

SYNTHESIS OF COMPOUND 1

100 mMoles of p-guanidinobenzoic acid is refluxed with 150 mMoles of freshly distilled thionyl chloride in the presence of 1 drop of dimethylforamide. When gas evolution ceases the excess thionyl chloride is removed exvacuo. The resulting hydrochloride salt of p-guanidinobenzoic acid chloride is then washed with ether to remove any residual reagent an dried exvacuo.

Then 110 mMoles of ethyl 4-hydroxybenzolyacetate is refluxed with 100 mMoles of the hydrochloride salt of p-guanidinobenzoic acid chloride in a suitable solvent such as pyridine or methylene chloride in the presence of a few crystals of DMAP. When the reaction has proceeded to completion as evidenced by thin layer chromatography the solvent is removed exvacuo. Then 500 ml of diethyl ether and 500 ml of water are added. The organic phase is then washed ×2 with 200 ml of 0.1N HCL. The aqueous phases are then combined and extracted with 200 ml of diethyl ether and dried. The desired ester Compound 2 is then purified by recrystallization from a suitable solvent.

Compound 2 is then catalytically hydrogenated at 50 psig hydrogen and 80 C in a Parr apparatus employing a chiral ruthenium-BINAP catalyst. Taber, D. F.; Silverberg, L.; (1991); *Tetrahedron Lett.*; 32:4227. The resulting Compound 3 is then purified by chromatography on silica or by recrystallization from a suitable solvent.

50 mMoles of phosphorus oxychloride in 50 ml of methylene chloride at −10 C is reacted with 100 mMoles of triethylamine and 100 mMoles of 2-chloroethylamine hydrochloride to form Compound 4. When the reaction has proceeded to completion the precipitated triethylamine hydrochloride is removed by filtration. Then 50 mMoles of Compound 2 (as the free base) and 150 mMoles of n-methylimidazole are added at −10 C and the reaction is allowed to warm to room temperature. After the reaction has proceeded to completion as monitored by TLC the solvent is removed exvacuo. The residue is washed with 300 ml of diethyl ether. The residue is then dried exvacuo. The desired product is then isolated as the hydrochloride salt by recrystallization from a suitable solvent. Alternatively the desired product may be purified by chromatography on silica.

EXAMPLE 2

Replacing ethyl 4-hydroxybenzoylacetate in the synthesis given for Compound 1 with ethyl 3-(4-hydroxy,3-chlorophenyl)-3-oxopropanoate will yield the drug shown below as Compound 5. The chlorine substituent in Compound 5 will slow the rate of solvolysis of the intermediate which is generated by the action of guanidinobenzoatase. This will allow for increased diffusion of the intermediate into the tumor cells and possibly enhanced antitumor potency.

Ethyl 3-(4-hydroxy,3-chlorophenyl)-3-oxo-propanoate may be readily synthesized by chlorination of ethyl 4-hydroxy-benzoylacetate. Alternatively, refluxing 3-chloro,4-hydroxy-acetophenone with sodium and diethyl carbonate will yield the desired product.

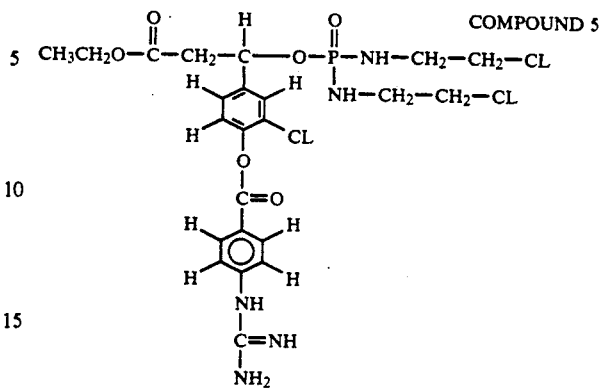

EXAMPLE 3

Replacing ethyl 4-hydroxybenzoylacetate in the synthesis given for Compound 1 with ethyl 3-(4-aminophenyl)-3-oxo-propanoate will yield the drug shown below as Compound 6.

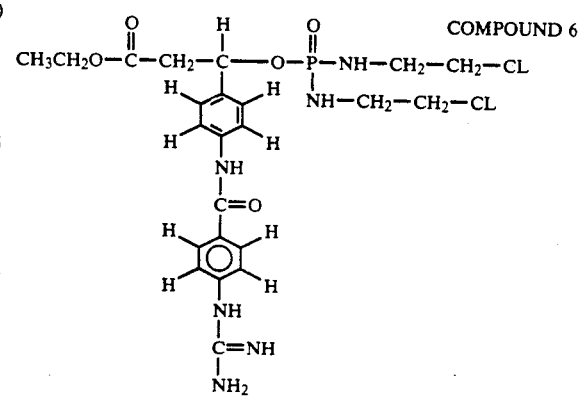

Ethyl 3-(4-amino-phenyl)-3-oxo-propanoate is readily synthesized from ethyl p-nitrobenzoylacetate by controlled catalytic hydrogenation of the nitro group with a suitable catalyst such as palladium on carbon or Raney nickel.

EXAMPLE 4

Compound 7 can readily be synthesized from the hydrochloride salt of Compound 6 by the action of a wide range of chlorinating reagents such as thionyl chloride or n-chlorosuccinimide. Alternatively, Compound 7 may be synthesized by replacing ethyl 3-(4-amino-phenyl)-3-oxo-propanoate with ethyl 3-(4-amino,3-chlorophenyl)-3-oxo-propanoate in the synthesis given for Compound 6.

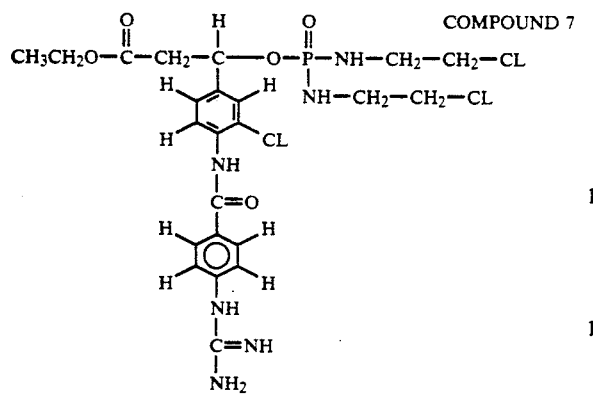

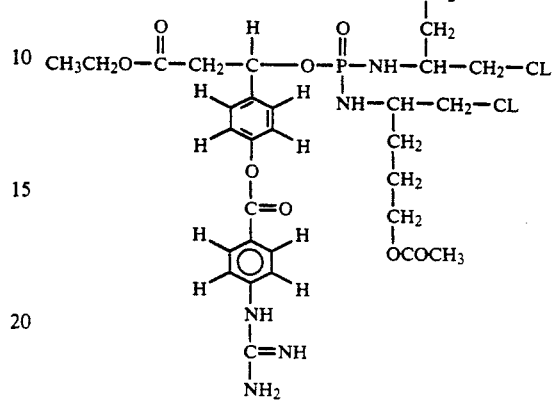

EXAMPLE 5

Compound 8 may be synthesized by substituting the chloroethylamine hydrochloride in the synthesis of Compound 1 with 50 mMoles of bis-(2-chloroethyl)amine hydrochloride and 50 mMoles of NH$_3$.

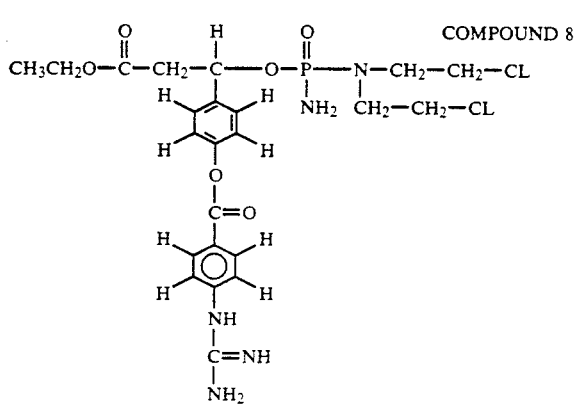

EXAMPLES 6-9

Compounds 9-12 may be synthesized by substituting the hydrochloride salt of 5-chloro,4-amino-pentyl acetate for 2-chloroethylamine hydrochloride in Examples 1-4 respectively. Chiral 5-chloro,4-amino-pentyl acetate may readily be synthesized by treatment of chiral pentahomoserine hydrochloride with 1 equivalent of acetic anhydride and a catalytic quantity of DMAP. The carboxylate group is then selectively reduced to the corresponding alcohol with borane. Yoon, N.; Pak, C.; Brown, H.; Krishnamurthy, S.; Stocky, T.; (1973) *J. Org. Chem.;* 38:2786. Treatment with thionyl chloride or HCL will yield the desired compound.

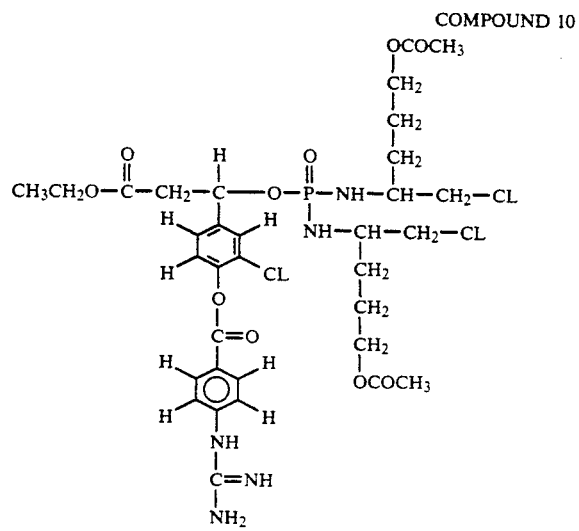

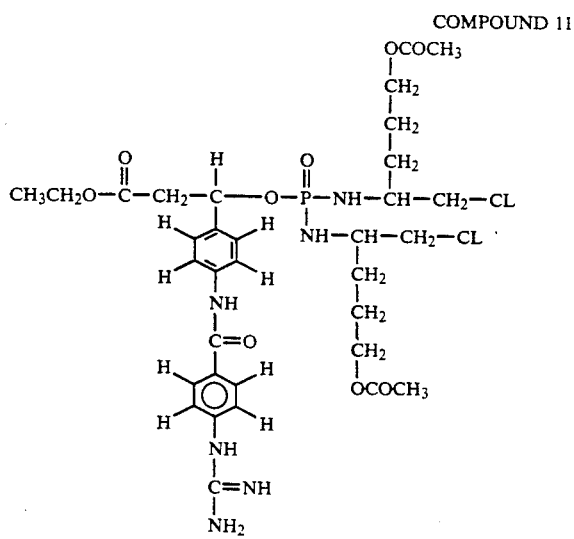

COMPOUND 12

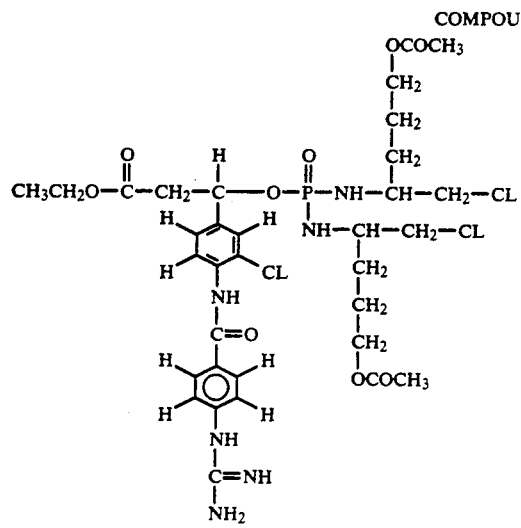

EXAMPLES 10-13

Compounds 13-16 may be synthesized by substituting the hydrochloride salt of 4-chloro,5-amino-pentyl acetate for 2-chloroethylamine hydrochloride in Examples 1-4 respectively. 4-chloro,5-amino-pentyl acetate may be synthesized by the epoxidation of 4-pentene-1-yl acetate with 3-chloroperoxy-benzoic acid. Treatment of the resulting epoxide with sodium azide will yield 4-azido,3-hydroxy-pentyl acetate. Catalytic hydrogenation with Raney nickel will yield 4-amino,3-hydroxy-pentyl acetate. Subsequent treatment with thionyl chloride or HCL will yield the desired 4-chloro,5-amino-pentyl acetate as the hydrochloride salt.

COMPOUND 13

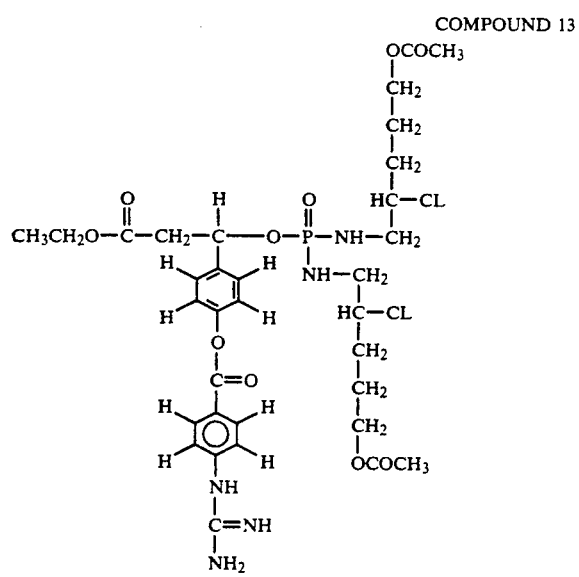

COMPOUND 14

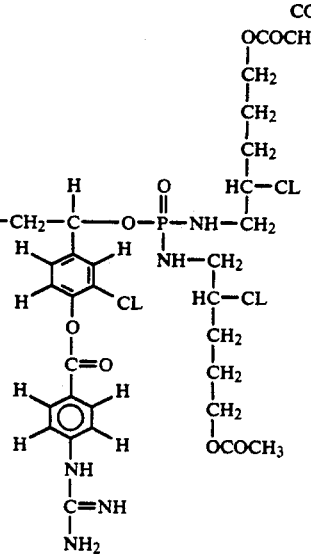

COMPOUND 15

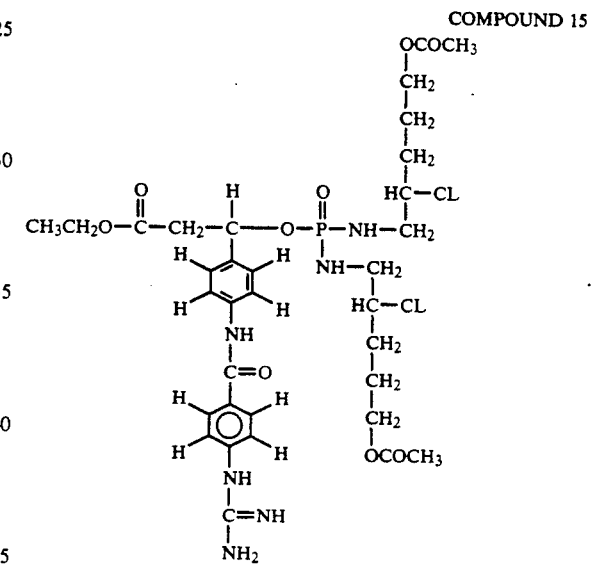

COMPOUND 16

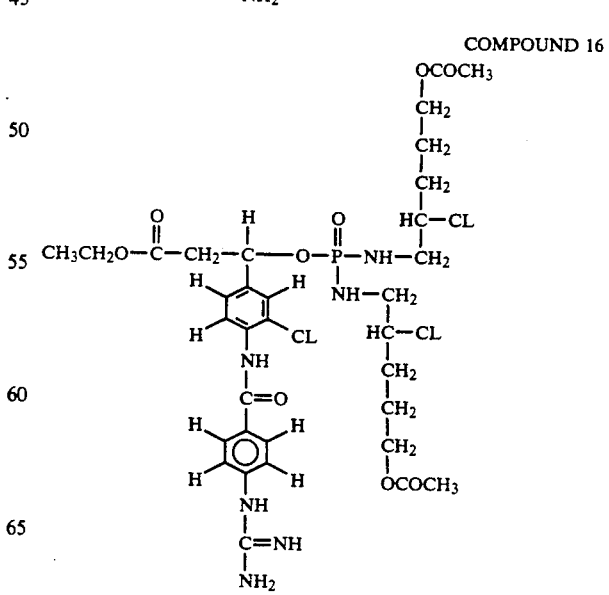

Compounds 9-16 will be converted by the action of GB on the surface of tumor cells into a potent bifunctional alkylating agent. In normal tissues which lack GB the compounds will be detoxified by nonspecific esterase activity.

EXAMPLE 14 and 15

Compound 17 and Compound 18 shown below are examples of nonabsorbable inhibitor of GB which is may be administer orally to a patient being treated with a GB selective antineoplastic drug in order to inactivate normal colonic GB.

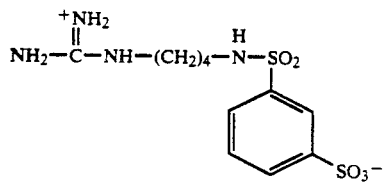

COMPOUND 17

Compound 17 may be synthesized by the reaction of agmatine sulfate with 1 equivalent of m-benzenedisulfonyl chloride in the presence of a catalytic amount of DMAP in an inert solvent followed by treatment with water. The compound may then be purified by recrystallization from a suitable solvent.

Compound 18 may be synthesized by the reaction of 2 equivalents of agmatine sulfate with 1 equivalent of m-benzenedisulfonyl chloride in the presence of a catalytic amount of DMAP in an inert solvent. The compound may then be purified by recrystallization from a suitable solvent and isolated as a hydrochloride or sulfate salt.

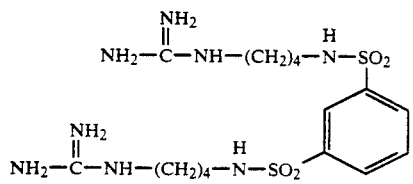

COMPOUND 18

GENERAL METHODS OF SYNTHESIS

The following are key intermediates in the synthesis of Compounds given by Formula 1 wherein R1-R11 and Y are as described for Formula 1.

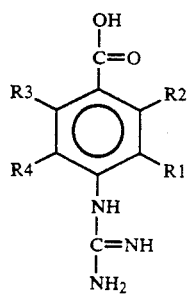

FORMULA 6

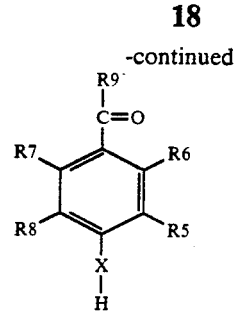

FORMULA 7

Compounds represented by Formulae 6 and 7 are known compounds which may be purchased or readily synthesized by one skilled in the arts of organic chemistry using routine methodologies.

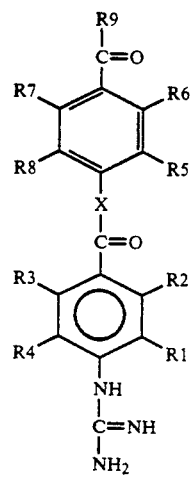

FORMULA 8

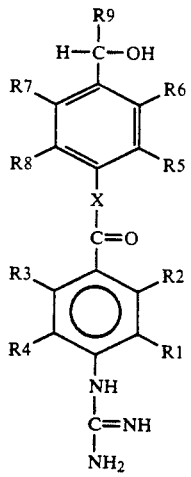

FORMULA 9

Compounds given by Formula 8 may be synthesized from compounds of Formula 7 and the acid chloride derivative of Formula 6 in an inert solvent. DMAP may be employed as a catalyst. The acid chlorides of Formula 6 are readily obtained by the action of a reagent such as thionyl chloride.

Compounds given by Formula 9 may be readily synthesized by the reduction of the compounds of Formula 8. This reduction may be effected by a variety of methods including catalytic hydrogenation with palladium on carbon or platinum dioxide. Enantioselective reduction may be effected by catalytic hydrogenation with a chiral Noyori catalyst. Reduction may also be effected by ammonia-borane. Noyori, R.; Ohkuma, T.; Kitamura, M.; (1987); *J. Am. Chem. Soc.;* 109:5856 Taber, D. F.; Silverberg, L.; (1991); *Tetrahedron Lett.;* 32:4227

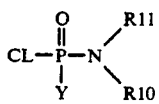 FORMULA 10

Compounds given by Formula 10 may be synthesized by the reaction in an inert solvent of phosphorous oxychloride with 1 equivalent of the hydrochloride of R10-NH-R11, and 1 equivalent of H—Y (or the hydrochloride) in the presence of a base such as triethylamine. The synthesis of the hydrochlorides of R10-NH-R11, and H—Y is trivial using routine techniques of organic chemistry.

Compounds given by Formula 1 may be synthesized by the reaction between compounds of Formula 9 and Formula 10 in an inert solvent. A catalyst such as n-methylimidazole may be employed. One skilled in the arts of organic chemistry will recognize many other routes to the synthesis of compounds of Formula 1.

GENERAL METHODS TO SYNTHESIZE COMPOUNDS OF FORMULA 5

Compounds of Formula 5 may be synthesized by reacting the desired guanidino-alkyl-amine with 1 equivalent of m-benzenesulfonyl chloride in an inert solvent. A catalyst such as DMAP may be employed. Then 1 equivalent of R is added in the presence of a suitable base. Note that R may be another equivalent of the guanidino-alkyl-amine, water, or a hydrophilic carrier such as polyethylene glycol. The carrier must possess a hydroxy or amino group which is able to react with the sulfonyl chloride.

Equivalents

Those skilled in the arts will recognize or be able to ascertain, using no more than routine experimentation, many equivalents to the specific materials and components described herein. Such equivalents are intended to be encompassed in the scope of the following claims.

I claim:

1. An antineoplastic compound of the structure: (A-C-B) wherein A is a substrate for an enzyme (Ea) which is enriched in the target tumor such that the enzymatic activity of this enzyme on A renders the compound toxic to a cell; wherein B is a substrate for one or more enzymes (Eb) which are present in normal tissues such that the enzymatic activity of this enzyme on B renders the compound nontoxic to a cell; and wherein C represents that portion of the compound molecule which is rendered toxic or nontoxic by the enzymatic activity of Ea or Eb.

2. A compound of claim 1 wherein Ea is Guanidinobenzoatase.

3. A compound of claim 2 wherein Eb is an esterase.

4. A compound which, when exposed to the enzymatic activity of Guanidinobenzoatase, is rendered toxic to a cell.

5. A compound of claim 4 of the following structure:

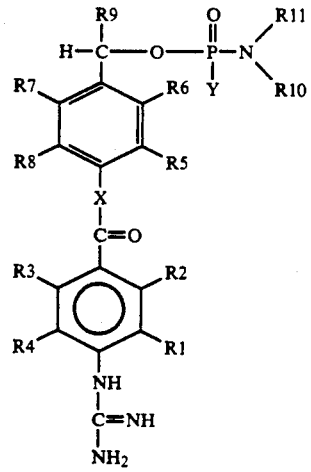

wherein R1, R2, R3, R4, are each selected from the group: H, Cl, F, Br; methyl, and —O—CH3;
X is O or NH;
R5, R6, R7, and R8 are selected from the group: H; Cl; F; CH3; —O—CH3; and —NO2;
R9 is H or —CH2—CO2—R13, wherein R13 is methyl, or ethyl,
R10 is —CH2—CHClR14, or —CHR14—CH2—Cl,
R11 is selected from the group: H; —CH2—CHClR14; —CHR14—CH2—Cl; or CH3,
Y is selected from the group: —NH3; —NH—CH2—CHClR14; —NH—CHR14—CH2—Cl; —OCH3; —CH3; CH3—N—CH2—CHClR14; and CH3—N—CHR14—CH2—Cl, wherein the total number of chlorine atoms attached to groups Y, R10 and R11 is equal to 2, 3, or 4;
wherein R14 is selected from the group: H; —CH2—CH2—CH2—O—CO—R15; CH2—CH2—CH2—NH—CO—R15; and —CH2—CH2—CH2—S—CO—R15; and wherein R15 is a methyl, ethyl, isopropyl, butyl, phenyl, or HO—CO—R15 is an amino acid.

6. A Compound of claim 5 in which X is —NH—.

7. A compound of claim 5 of the following structure:

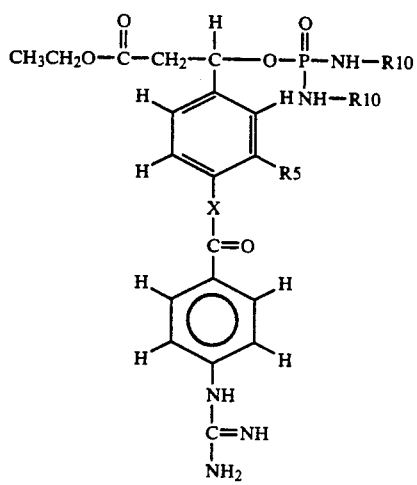

wherein X is O, or NH; R5 is H or a halogen; and R10 is selected from the following group:

—CH₂—CH₂—CL, A
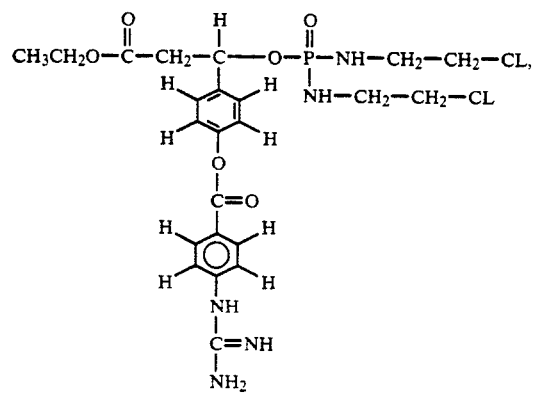
8. A compound of claim 5 selected from the following structures A-M shown below:
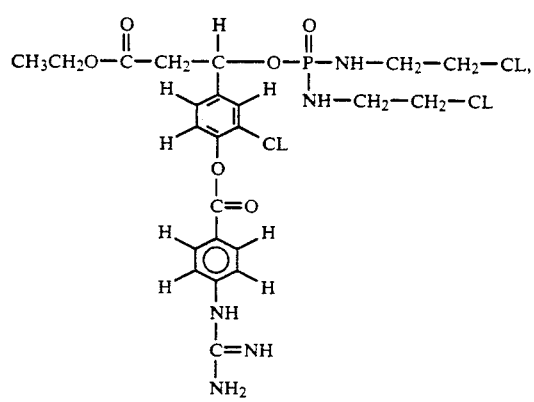
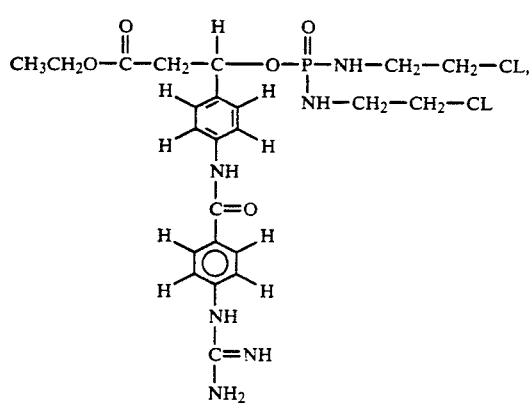
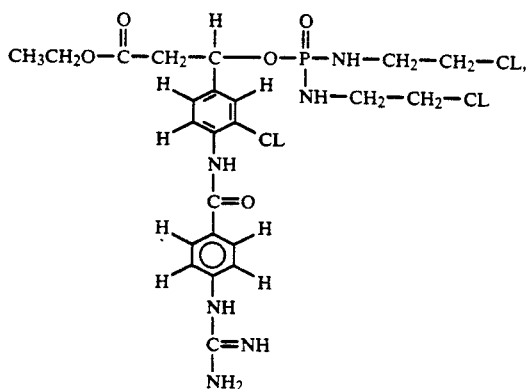
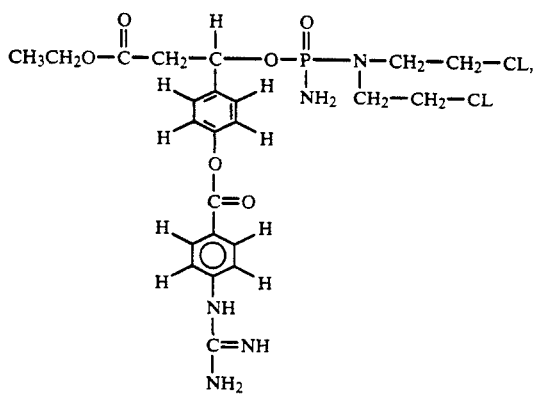
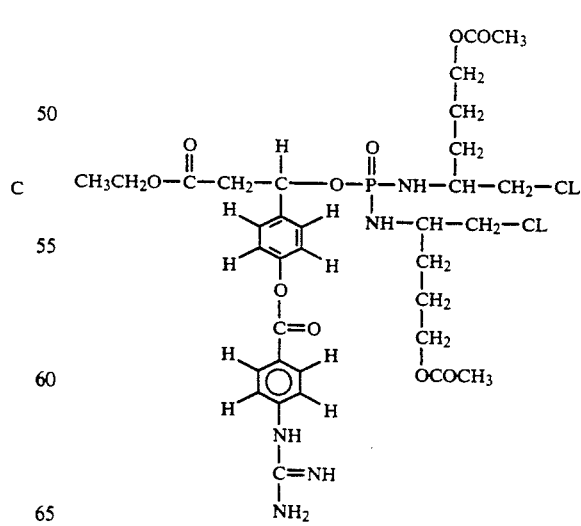

G
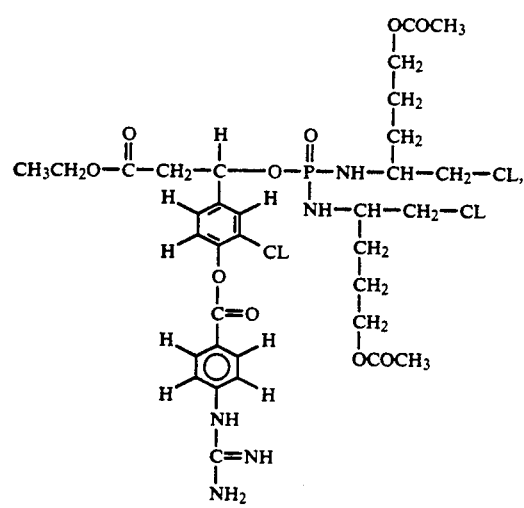
J
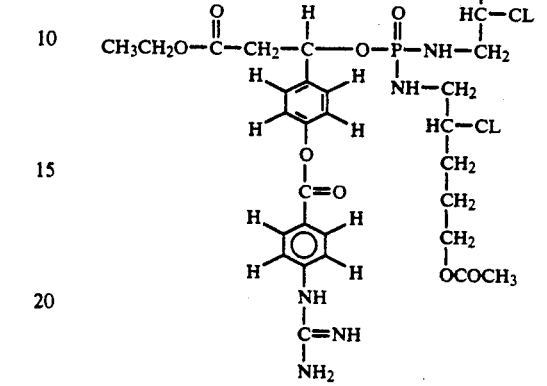
H
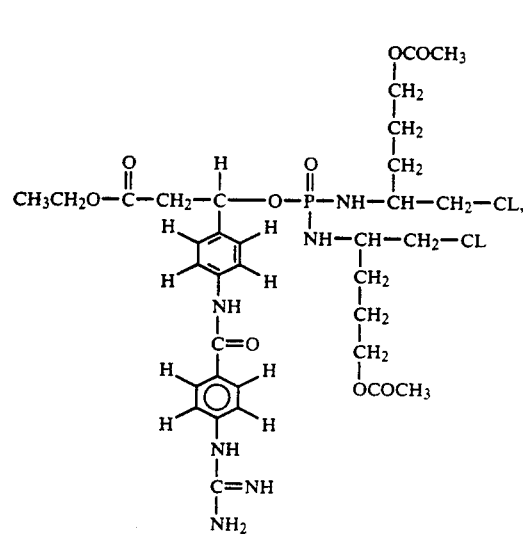
K
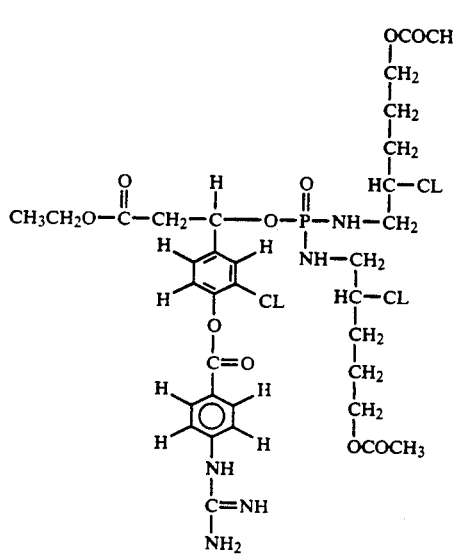
I
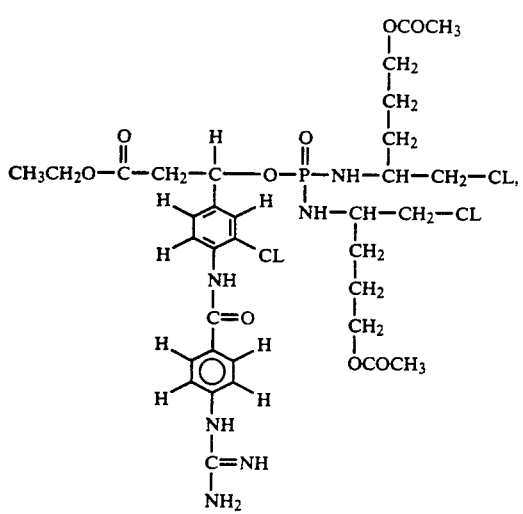
L
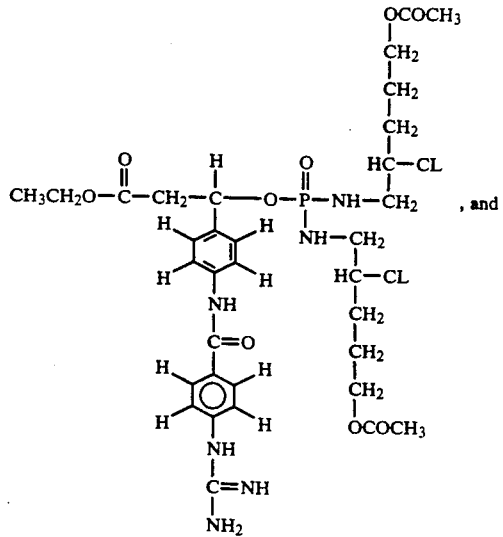
, and

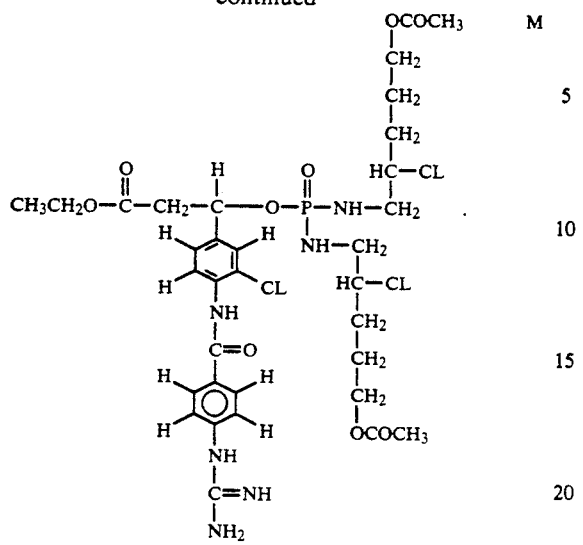
* * * * *